(12) United States Patent
Assi et al.

(10) Patent No.: US 6,332,991 B1
(45) Date of Patent: Dec. 25, 2001

(54) CONTAINER AND METHOD FOR CROSS-LINKING COMPOSITE MATERIALS ON DENTAL PROSTHESIS

(75) Inventors: Silvia Assi, Via Oberdan, 55, 20047 Brugherio; Antonio Tissi, Peschiera Borromeo, both of (IT)

(73) Assignee: Silvia Assi, Brugherio (IT)

( * ) Notice: Subject to any disclaimer, the term of this patent is extended or adjusted under 35 U.S.C. 154(b) by 0 days.

(21) Appl. No.: 09/424,714

(22) PCT Filed: Apr. 29, 1998

(86) PCT No.: PCT/EP98/02535

§ 371 Date: Nov. 29, 1999

§ 102(e) Date: Nov. 29, 1999

(87) PCT Pub. No.: WO98/53756

PCT Pub. Date: Dec. 3, 1998

(30) Foreign Application Priority Data

May 29, 1997 (IT) .............................................. MI97A1267

(51) Int. Cl.[7] .............................. A61C 13/16; A61C 13/20
(52) U.S. Cl. .................................. 264/16; 249/54; 249/83; 249/142; 249/166; 264/19; 264/221; 264/222; 425/2; 425/127; 433/34; 433/167
(58) Field of Search ................................. 264/16, 19, 221, 264/222; 425/2, 127; 249/54, 83, 142, 166; 433/34, 167

(56) References Cited

FOREIGN PATENT DOCUMENTS

| 513 972 | 5/1954 | (BE) . |
| 40 05 570A1 | 8/1991 | (DE) . |
| 40 28 728A1 | 3/1992 | (DE) . |
| 2 280 358 | 2/1976 | (FR) . |

Primary Examiner—Leo B. Tentoni
(74) Attorney, Agent, or Firm—Guido Modiano; Albert Josif; Daniel O'Byrne

(57) ABSTRACT

A container for cross-linking composite materials on dental bridges and arches and on individual teeth, comprising: a plurality of plate-like elements which can be stacked and clamped together, at least one of the plate-like elements, which is internal to the plurality of plate-like elements, being constituted by a plurality of blocks which can be removed independently of each other to form an area which is suitable to constitute a mold into which it is possible to place a metallic structure on which the elements of a dental prosthesis are to be formed, the at least one of the plate-like elements and a plate-like element that is adjacent thereto in an upward region and constitutes the top plate-like element of the container being both made of a material which is transparent to light.

14 Claims, 3 Drawing Sheets

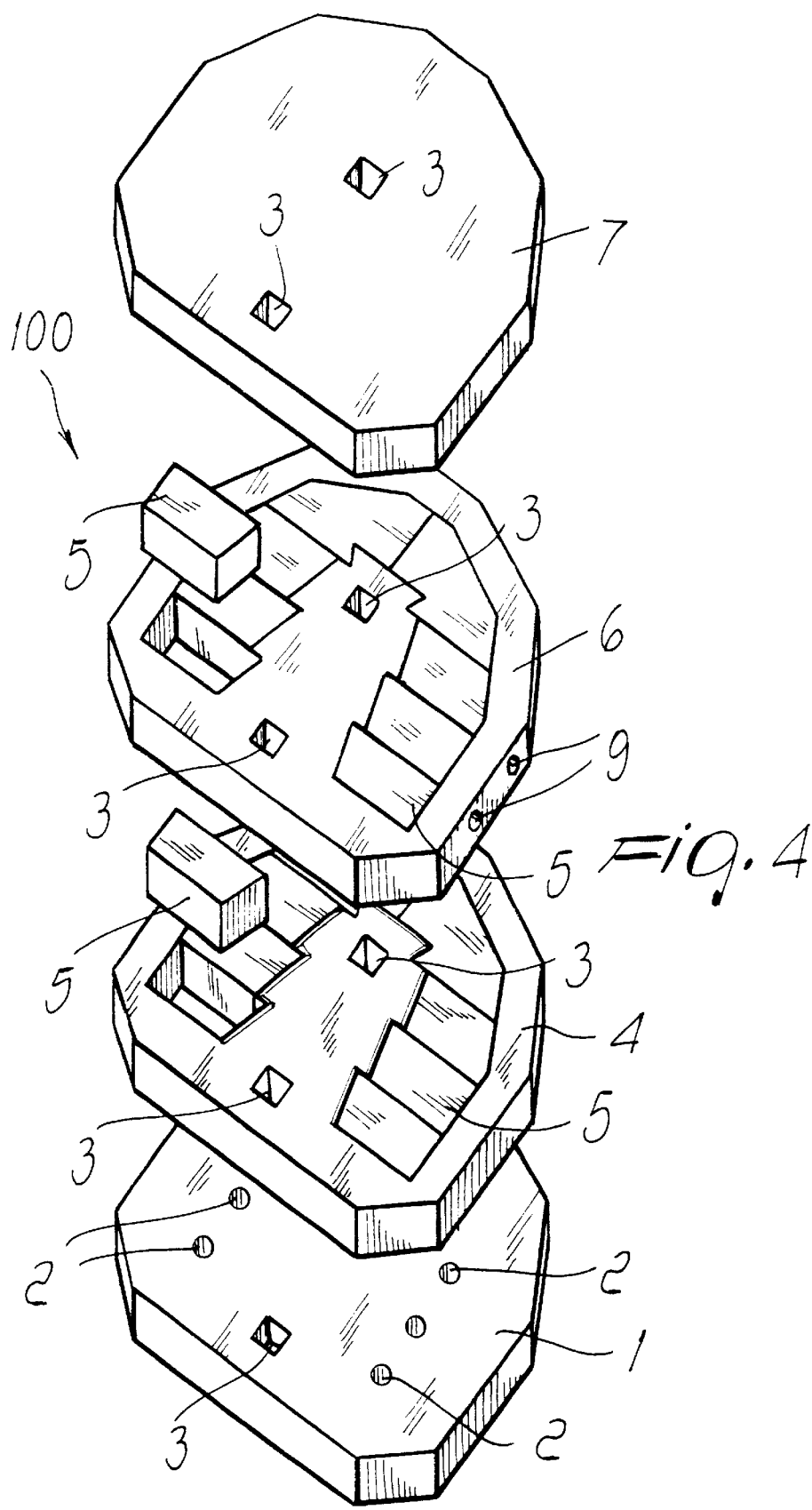

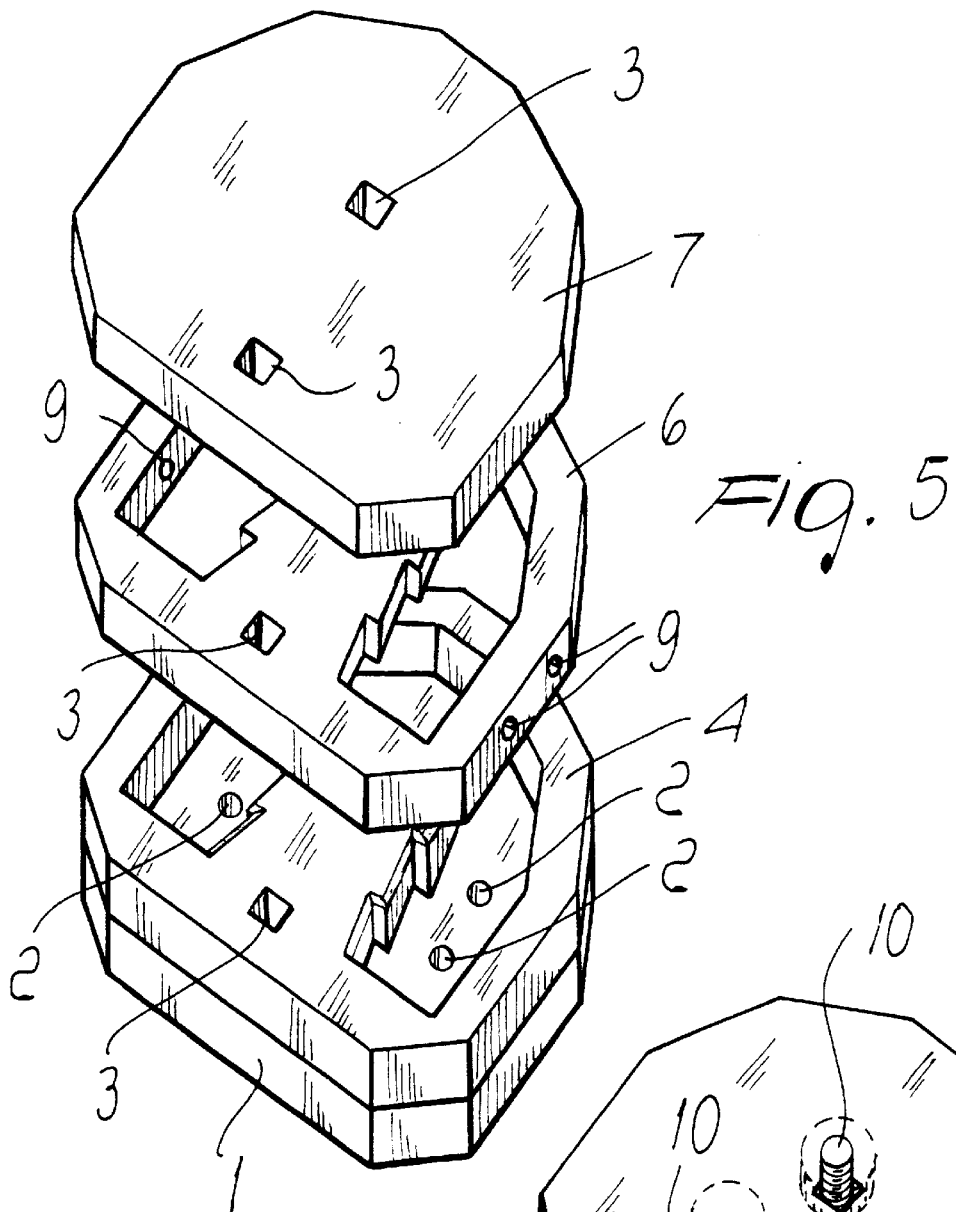
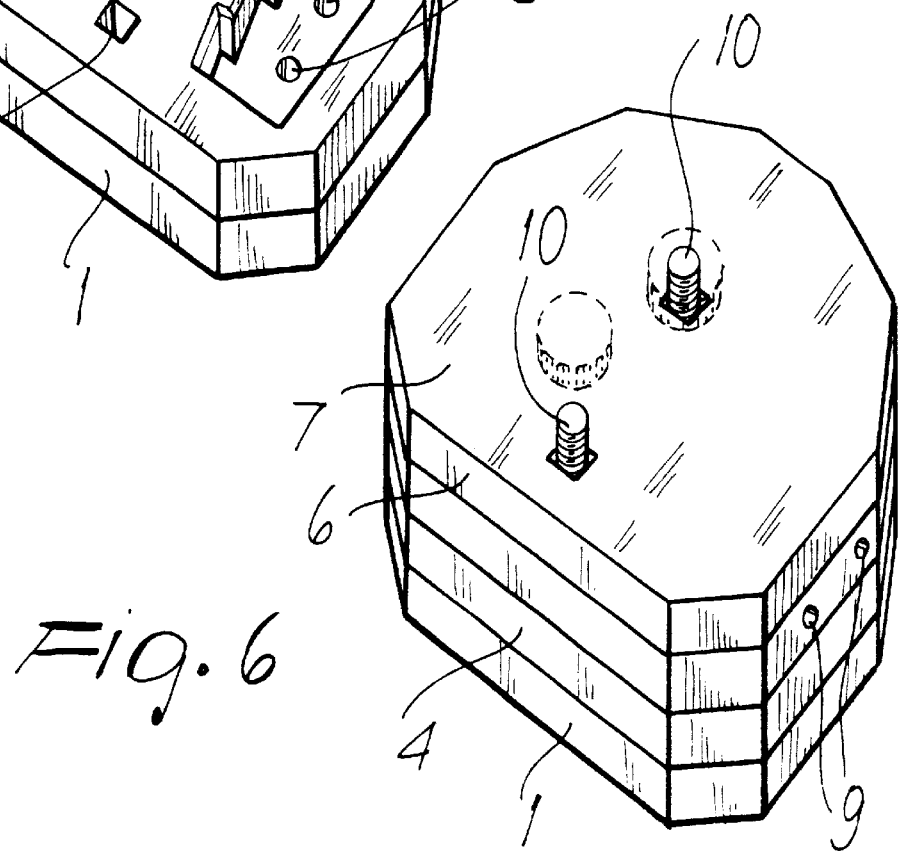

CONTAINER AND METHOD FOR CROSS-LINKING COMPOSITE MATERIALS ON DENTAL PROSTHESIS

TECHNICAL FIELD

The present invention relates to a container and a method for cross-linking composite materials on dental crowns, bridges and arches, particularly for use with photopolymerizing lamps.

More particularly, the invention relates to a container and to a method for modeling teeth in the field of prosthodontics.

BACKGROUND ART

It is known that the following method is used in order to perform the cross-linking of dental bridges, crowns or entire arches meant to replace missing teeth of a patient:

the dental surgeon prepares pillars (filed natural or artificial teeth) which support the entire prosthesis;

then takes the impression (in silicone or other material) and gives it to the prosthodontics laboratory;

the dental technician pours plaster into the impression so as to obtain the model on which the prosthesis is to be built;

the metallic supporting structure is then prepared on the model (which represents the mouth of the patient).

A photopolymerizable composite material is applied directly to the metallic structure that constitutes the support for the teeth forming the dental prosthesis to be produced; said material is modeled manually in order to produce the correct shape and size of the individual teeth composing the prosthesis.

This manual treatment of the composite material, besides being extremely difficult from the practical point of view since the composite material can sometimes be very hard and therefore requiring highly specialized personnel, is considerably expensive in terms of time and costs.

In order to model a prosthesis which is constituted for example by a single tooth or by a pair of teeth, i.e., a prosthesis that covers a limited portion of the dental arch, this drawback can be obviated by providing a plaster template which is used to shape the composite material.

This solution, however, is not applicable if a prosthesis is to be obtained that covers a considerable extent of the dental arch, since the plaster pattern must adhere and be shaped according to the metallic supporting structure but its rigidity prevents it from doing so.

A partial solution to this problem might consist in providing the plaster pattern in two or three parts, but it has been observed that in this case it is very difficult to adjust each part of the plaster pattern with the same pressure and in the same position in order to achieve correct shaping of the composite material.

DISCLOSURE OF THE INVENTION

The aim of the present invention is to provide a container for molding teeth which allows to model both individual teeth and very extensive bridges or entire dental arches by using the container itself as a mold.

Within the scope of this aim, an object of the present invention is to provide a container for molding teeth previously modeled in wax instead of directly using the composite material on the metallic supporting structure.

Another object of the present invention is to provide a container for molding teeth which can be exposed directly to photopolymerizing light.

Another object of the present invention is to provide a container for modeling teeth which allows to quickly correct any errors in color or characterization.

Another object of the present invention is to provide a container for modeling teeth which ensures a quality of the finished work which is equal to, or better than, the conventional manual method.

Another object of the present invention is to provide a method for molding teeth which allows to use a specifically provided modeling container which can be exposed to photopolymerizing light.

Another object of the present invention is to provide a tooth molding method which allows to obtain a mold of the wax model which can be tested directly in the patient's mouth so as to allow to easily correct any imprecisions thereof.

Another object of the present invention is to provide a container and a method for molding teeth which are highly reliable, relatively easy to provide and at low costs.

This aim, these objects and others which will become apparent hereinafter are achieved by a container for cross-linking composite materials on dental bridges and arches and on individual teeth, characterized in that it comprises a plurality of plate-like elements which can be stacked and clamped together, at least one of said plate-like elements, which is internal to said plurality of plate-like elements, being constituted by a plurality of blocks which can be removed independently of each other to form an area which is suitable to constitute a mold into which it is possible to place a metal structure wherefrom a dental prosthesis is to be obtained, said at least one of said plate-like elements and a plate-like element that is adjacent thereto in an upward region and constitutes the top plate-like element of said container being both made of a material which is transparent to light.

This aim is also achieved by a method for cross-linking composite materials on teeth of bridges and dental arches by means of a container, characterized in that it comprises the steps of:

applying wax to a metallic supporting structure for a tooth, bridge or entire dental arch and manually modeling the wax so as to reconstruct the shape of the intended teeth;

inserting said metal structure, with modeled wax applied thereto, in said container;

injecting transparent silicone into said container, so as to surround said wax-covered metallic structure, embedding said structure in the silicone;

mutually clamping the plate-like elements constituting said container in order to compress said transparent silicone and make it adhere to the wax that covers said metallic structure, so that said silicone, by curing, assumes the shape of the modeled wax, obtaining the mold;

opening said container, removing the wax from said metallic structure and filling with composite materials the space freed by the removal of said wax; and placing said metallic structure, with the composite material on it, back into said container and exposing said container to a photopolymerization machine in order to cure said composite materials and produce the intended prosthesis.

BRIEF DESCRIPTION OF THE DRAWINGS

Further characteristics and advantages of the container and the method for cross-linking composite materials on
} dental prostheses according to the present invention will become apparent from the following detailed description of a preferred but not exclusive embodiment of the device, illustrated only by way of non-limitative example in the accompanying drawings, wherein:

FIG. 4 is an exploded perspective view of the container according to the present invention;

FIG. 5 is a partially exploded perspective view of the container according to the present invention; and FIG. 6 is a perspective view of the container according to the present invention.

WAYS OF CARRYING OUT THE INVENTION

Figure 1:
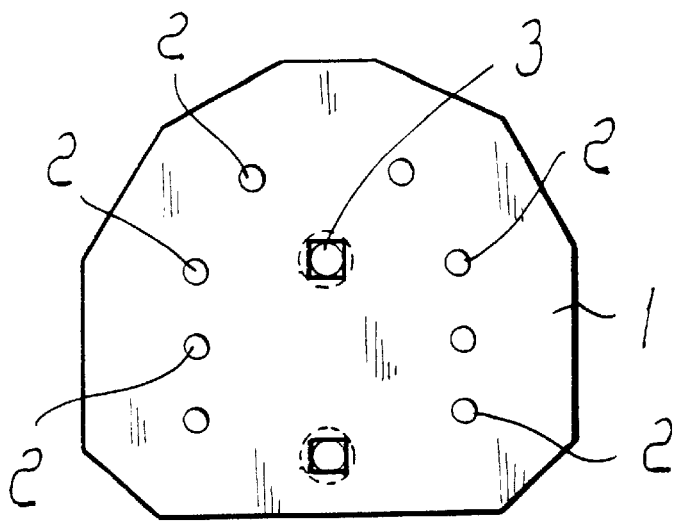
FIG. 1 is a plan view of a first element that constitutes the container according to the present invention.

With reference to the above figures, the container according to the present invention, generally designated by the reference numeral 100, comprises a first plate-like element or base element 1 (see FIG. 1) provided with a plurality of small holes 2 and with at least two larger holes 3 (but preferably four) which are meant to allow the passage of a pair of traction elements which are described hereinafter.

A second plate-like element 4 is glued to the first element 1, and an inner region thereof may be divided into a plurality of blocks 5 which can be separately removed and has at least a pair of holes (similar to the holes 3 of the first plate-like element and therefore designated by the reference numeral) which arrange themselves at the holes 3 of the first plate-like element 1.

The region formed by the blocks 5 has a shape which corresponds to an imaginary dental arch of a patient. The blocks can be shaped in any manner which is not limited to the shape shown in FIG. 2, and their dimensions may likewise be variable.

The blocks 5 are inserted in a central region 8 of the plate-like element 4, so that if one of the blocks is removed the remaining blocks remain in place.

The small holes 2 formed in the base plate-like element 1 are located at the blocks 5 so that when the first and second plate-like elements 1 and 4 are glued together it is possible to remove the blocks 5 in the chosen position simply by acting through the small holes 2 with a pointed object.

Accordingly, the number of holes 2 must be equal to, or greater than, the number of blocks 5.

Figure 2:
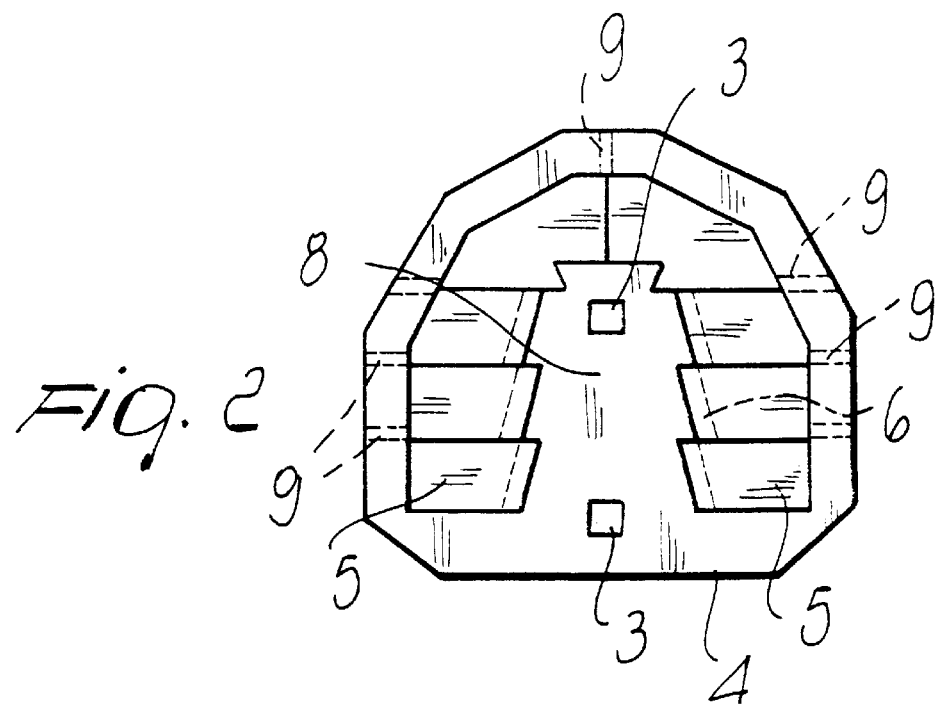
FIG. 2 is a plan view of a second element and of a third element constituting the container according to the present invention.

A third plate-like element 6 is also provided which is similar to the second plate-like element 4 and is therefore also shown in FIG. 2. In particular, the third plate-like element 6 forms blocks 5 which are shaped like the blocks 5 of the second plate-like element 4, except that in the fixed central body the third plate-like element 6 has upper edges (adjacent to the blocks) which are chamfered, so as to form undercuts with the corresponding blocks whose functions will be defined hereinafter.

Again in the third plate-like element 6 at each block 5 discharge channels 9 are provided which allow to discharge the transparent silicone used during a step of the method as described hereinafter.

Figure 3:
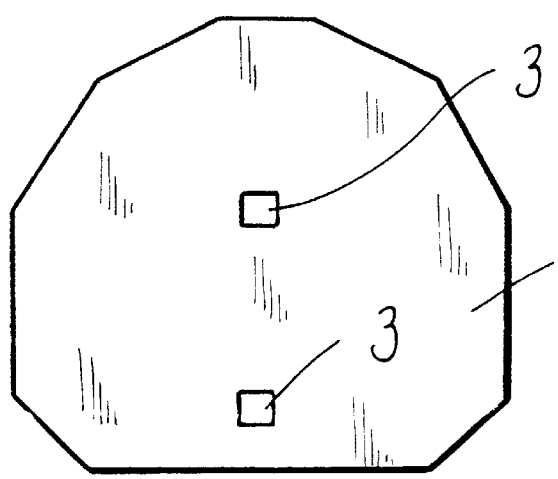
FIG. 3 is a plan view of a fourth element constituting the container according to the present invention.

A fourth and last plate-like element 7, shown in FIG. 3, is meant to be arranged on the third plate-like element 6.

The third plate-like element 6 and the fourth plate-like element 7 are both provided with the same holes 3 formed in the first and second plate-like elements 1 and 4.

Said holes 3, which are mutually coaxial when the four plate-like elements are mutually stacked, allow the passage of coupling elements which are advantageously constituted for example by a plurality of traction elements 10 which have the purpose of ensuring the mutual clamping of the four plate-like elements.

The traction elements 10 inserted in the holes 3 are then clamped by means of wing nuts or plain nuts.

The multilayer container described above is conveniently made of plastics, such as for example polycarbonate or plexiglass or in any case of a material which can be transparent to light.

In particular, the third and fourth plate-like elements 6 and 7 must be made of transparent material in order to allow the passage of light for the photopolymerization step described hereinafter.

The first plate-like element 1 and the second plate-like element 4 need not be made of transparent and plastic material.

With reference to the above figures, the method for using the container according to the invention described above is as follows.

First of all, a layer of wax is applied to a metallic supporting structure (not shown) of the prosthesis to be produced, which is obtained in a known manner; the layer is sculpted manually in order to produce the shape of the teeth to be reconstructed.

The metallic structure, with the wax thus modeled, is then placed on the first plate-like element 1 after arranging a certain amount of silicone on the element 1, so that the apex of the wax teeth (not shown) lies below (by a few millimeters) the fourth plate-like element 7.

The metallic supporting structure rests on a silicone base which is arranged on the first plate-like element 1 at the blocks 5 removed beforehand from the plate-like element 4 superimposed on the element 1.

The blocks 5 are removed from the element 4 by acting through the small holes 2 formed in the base plate-like element 1, so as to remove the blocks corresponding to the portion to be reconstructed of the dental arch of the patient.

When the supporting structure is placed on the base element 1, whereon the plate-like element 4 is superimposed, the plate-like element 6 is positioned, superimposing said blocks 5 on the blocks 5 of the plate-like element 4. At this point, silicone or other suitable transparent material is injected.

The transparent silicone deposits around the metallic structure, saturating the plate-like element 6 and filling the above mentioned undercuts.

The fourth plate-like element 7 is then positioned.

The four plate-like elements 1, 4, 6 and 7 are then mutually clamped by means of the traction elements 10, so that the transparent silicone adheres to the sculpted wax that covers the metallic supporting structure.

The excess transparent silicone flows out of the container 100 by means of the channels 9 formed in the third plate-like element 6 at the blocks 5.

When the transparent silicone cures, the container 100 is opened, simultaneously removing the third and fourth plate-like elements 6 and 7; since said undercuts and the discharge channels are present, they act as retention elements for the transparent silicone, so that when opening the container 100 the silicone remains coupled to the third and fourth plate-like elements 6 and 7 and does not remain stuck to the wax teeth. The transparent silicone has thus assumed the shape of the pattern previously made of wax.

The wax is then removed with hot water or steam and the conventional composite photopolymerizable material (opaque dentin) is applied between the metallic structure and the transparent silicone. The container 100 is then closed again, by means of the traction elements 10, and in this manner the composite material occupies the space of the wax, i.e., the shape and the dimensions of the previously sculpted teeth.

The container 100 is then placed in a photopolymerizing machine, where the rays of light pass through the third and fourth transparent plate-like elements 6 and 7 and strike the metallic structure containing the composite material, which is photopolymerized and cures.

Once the polymerization of the opaque dentin is complete, the resulting prosthesis is extracted from the container: first of all, a thin layer of opaque dentin is removed by means of diamondized mills and then the metallic structure, with the first composite thereon, is reinserted and an additional enamel composite is applied in the space left by the removed material. The container 100 is closed again and reinserted in the photopolymerizing machine. Once the polymerization of the second layer of composite has ended, the resulting prosthesis is extracted.

In practice it has been observed that the container and the method according to the present invention fully achieve the intended aim, since they allow to apply wax to the metallic supporting structure instead of directly applying the composite material. This leads to an extreme simplification of the procedure for the manual sculpting of the teeth to be reconstructed.

Sculpting the composite is an extremely time-consuming process requiring highly specialized personnel, differently from what occurs instead for wax sculpting.

The advantage of being able to sculpt wax therefore automatically leads to a saving in terms of time and costs, as well as to the possibility to test the prosthesis made of wax directly in the patient's mouth so as to be able to correct any imperfections.

Moreover, the fact that a silicone mold with the shape of the teeth has been provided facilitates and shortens the rebuilding of prosthesis if it has a coloring that does not match the intended one.

It should also be observed that in the conventional direct modeling of the composite material on the metallic structure it is necessary to subsequently apply a gel to eliminate the oxygen of the composite: this is not necessary with the method, and the container according to the invention, since the pressure applied to the arch by the fastening of the plate-like elements prevents air from being trapped in the composite material.

The container and the method thus conceived are susceptible of numerous modifications and variations, all of which are within the scope of the inventive concept.

Thus, for example, as shown, the shape, the number and the size of the blocks 5, as well as the shape, the number and the dimensions of the plate-like elements may differ from what has been shown in the different figures.

Likewise, the number of plate-like elements need not be limited to the one described above.

Likewise, the traction elements 10 are shown as having a square cross-section, but nothing forbids to change their cross-section.

The second and third plates may be made in a single piece as well as in a plurality of pieces. In practice the border regions of the second and third plates may be split in a plurality of pieces to facilitate the opening of the container.

The blocks 5, as before said, may be provided or not. Such blocks 5 allow the user to save filling material which must be poored in the mold. The fact of having the blocks 5 is thus purely an economical advantage.

Nothing changes if the plates 4 and 6 are made in a single piece, internally emptied.

Finally, all the details may also be replaced with other technically equivalent elements.

In practice, the materials employed, so long as they are compatible with the specific use, as well as the dimensions, may be any according to requirements and to the state of the art.

What is claimed is:

1. A container for cross-linking photopolymerizable materials on dental bridges and arches and on individual teeth, comprising a plurality of plate-like elements which are adapted to be stacked and clamped together, at least one of said plate-like elements, which is internal to said plurality of plate-like elements, having an area in the form of a mold adapted to receive a supporting structure whereon the elements of a dental prosthesis are to be formed, said at least one of said plate-like elements and a plate-like element that is adjacent thereto in an upward region and constitutes the top plate-like element of said container being both made of a material which is transparent to light, said multiple plate-like elements being mutually connected and clamped by a plurality of traction elements which pass through coaxial holes formed in said mutually stacked plate-like elements.

2. A container according to claim 1, wherein said plurality of plate-like elements comprises four plate-like elements which are adapted to be mutually superimposed and clamped.

3. A container according to claim 1, comprising a first plate-like element which has a plurality of holes, a second plate-like element which is superimposed thereon and an inner region of which is constituted by a plurality of blocks which are adapted to be removed independently of each other, a third plate-like element which is identical to said second plate-like element and a fourth plate-like element.

4. A container according to claim 3, wherein said blocks of said second and third plate-like element are arranged at said holes formed in said first plate-like element.

5. A container according to claim 3, wherein the number of said holes of said first plate-like element is equal to the number of blocks of said second and third plate-like elements.

6. A container according to claim 3, wherein said blocks of said second and third plate-like element are locked between an edge of said plate-like elements and a central region thereof.

7. A container according to claim 6, wherein in the central region of said third plate-like element, the edges of its upper surface that are adjacent to the blocks are chamfered, said chamfered regions forming undercuts when said third plate-like element is coupled to said fourth plate-like element.

8. A container according to claim 3, wherein said third plate-like element is provided with channels at each one of said blocks constituting an internal region thereof, said channels being directed radially toward the edge of said third plate-like element.

9. A container according to claim 1, wherein said plurality of traction elements include a traction element which passes centrally through said mutually stacked plate-like elements and which is surrounded by said area in the form of the mold having a shape which corresponds to an imaginary dental arch of a patient.

10. A container according to claim 3, wherein said third and fourth plate-like elements are made of a material which is transparent to light.

11. A method for cross-linking composite materials on dental crowns, bridges and arches by of a container comprising: a plurality of plate-like elements which are adapted to be stacked and clamped together; at least one of said plate-like elements being internal to said plurality of plate-like elements and having an area in the form of a mold capable of receiving a metallic structure whereon the elements of a dental prosthesis are to be formed, said at least one of said plate-like elements and a plate-like element that is adjacent thereto in an upward region and constitutes the top plate-like element of said container being both made of a material which is transparent to light; and said multiple plate-like elements being mutually connected and clamped by a plurality of traction elements which pass through coaxial holes formed in said mutually stacked plate-like elements; the method comprising the steps of:

applying wax to a metallic structure for supporting a tooth, a bridge or an entire dental arch and manually sculpting the wax so as to reconstruct the shape of the intended teeth;

inserting said metallic structure, whereto sculpted wax has been applied, in said container;

injecting transparent silicone into said container, so as to surround said wax-covered metallic structure, embedding said structure in the silicone;

mutually clamping the plate-like elements constituting said container in order to compress said transparent silicone and make it adhere to the coveting wax of said metallic structure, so that said silicone, by curing, takes the shape of the modeled wax, obtaining the mold;

opening said container, removing the wax from said metallic structure and filling with composite material the space left free by the removal of said wax; and placing said metallic structure, with the composite material thereon, back into said container and exposing said container to a photopolymerization machine in order to cure said composite materials and produce the intended prosthesis.

12. A method according to claim 11, wherein the step of inserting said metallic structure, with the wax applied thereto, into said container comprises the step of:

resting said metallic structure, with the sculpted wax, on the first plate-like element.

13. A method according to claim 11, wherein said step of injecting transparent silicone is preceded by a step for positioning the third plate-like element.

14. A method according to claim 13, wherein said step of positioning said third plate-like element is followed by a step for positioning the fourth plate-like element preceding the clamping step.

* * * * *